United States Patent [19]

Pozo

[11] Patent Number: 4,719,793
[45] Date of Patent: Jan. 19, 1988

[54] HARDNESS TESTING APPARATUS
[75] Inventor: Jaime F. Pozo, Chicago, Ill.
[73] Assignee: AMSTED Industries Incorporated, Chicago, Ill.
[21] Appl. No.: 938,791
[22] Filed: Dec. 8, 1986
[51] Int. Cl.⁴ .............................................. G01N 3/48
[52] U.S. Cl. ...................................................... 73/81
[58] Field of Search .................. 73/81, 82, 83, 85, 78, 73/79

[56] References Cited

U.S. PATENT DOCUMENTS

| | | | |
|---|---|---|---|
| 1,354,218 | 9/1920 | Schneider | 73/81 |
| 2,850,894 | 9/1958 | Clark, Sr. | 73/83 |
| 3,295,363 | 1/1967 | Delporte | 73/81 |
| 4,164,141 | 8/1979 | Sandor et al. | 73/81 |
| 4,635,471 | 1/1987 | Rogers et al. | 73/81 |

Primary Examiner—Stewart J. Levy
Assistant Examiner—Robert R. Raevis
Attorney, Agent, or Firm—Edward J. Brosius; Charles E. Bouton

[57] ABSTRACT

The present invention provides an apparatus and method for measuring the hardness of a metal object such as a railway wheel. The wheel is rolled along a rail to a notched receiving assembly into which the wheel is lowered to stabilize the wheel in a longitudinal direction. A frame with a bracing device is then pressed against the wheel hub to stabilize the wheel in a lateral direction. A secondary frame including both a grinding device and a hardness testing device is then swung about a pivot axis such that the grinding device grinds a section of the metal railway wheel. Upon the continuation of the pivoting movement of the secondary frame, a hardness testing device is brought into alignment with the ground section of the railway wheel whereupon the hardness test of the wheel is performed.

5 Claims, 2 Drawing Figures

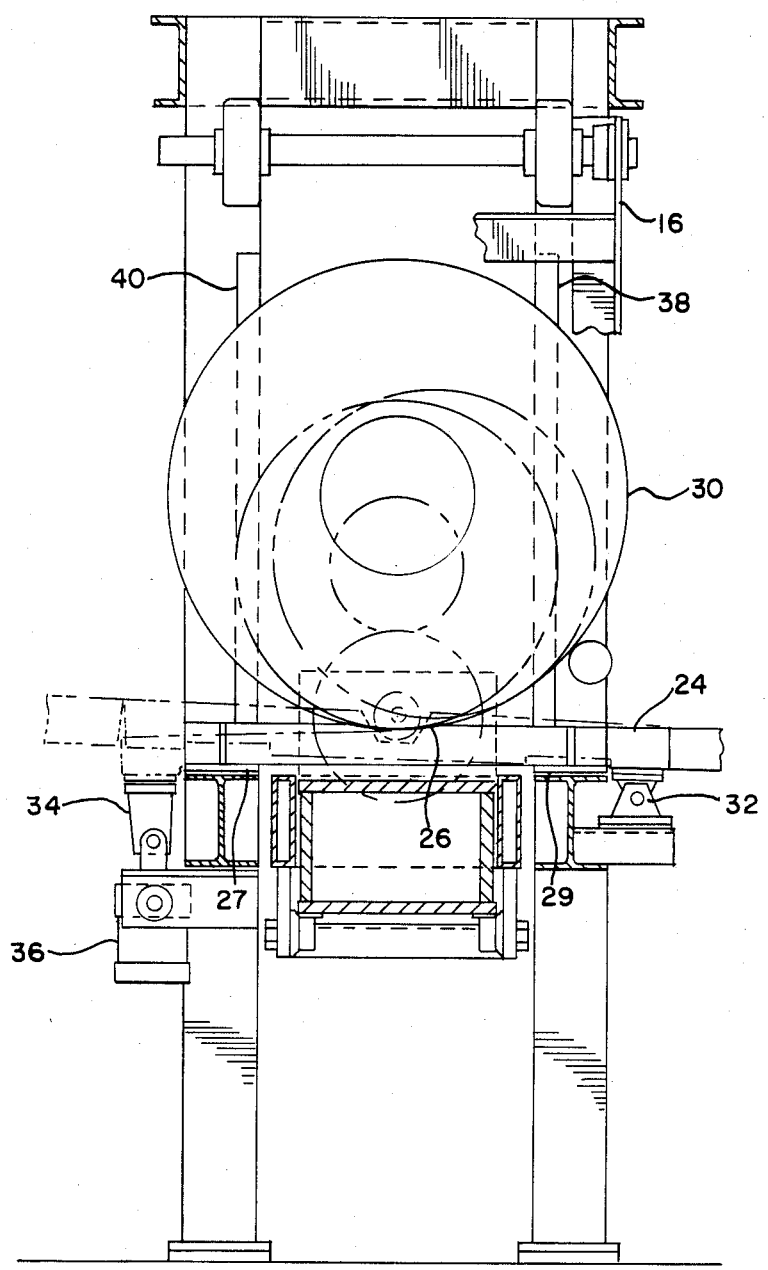

HARDNESS TESTING APPARATUS

BACKGROUND OF THE INVENTION

The present invention relates generally to hardness testing devices and, more particularly, to a hardness testing device having a grinding apparatus and hardness testing apparatus mounted on a frame about a single pivot axis.

Hardness testing apparatus for determining the Brinell hardness of metal objects such as railway wheels are known, one of which is disclosed in U.S. Pat. No. 4,164,141, assigned to the assignee of the present invention. Such an apparatus, while providing accurate hardness determinations, is somewhat complicated in the handling steps required to move the railway wheel into the testing device, accomplish the test and then move the railway wheel out of the device. In the referenced patented device, the railway wheel to be tested must be raised by an elevator assembly into contact with a grinding device, and then raised into contact with Brinell testing heads. Upon completion of the hardness test, the wheel is lowered by the elevator assembly back onto the rail, whereupon the locking devices are removed from contact with the wheel and the wheel is pushed from the testing apparatus. Due to the nature of the lifting devices required for the wheel, this test has proved time consuming and an improved method and apparatus for determining the hardness of railway wheels has been desired.

SUMMARY OF THE INVENTION

It is an object of the present invention to provide an improved method and apparatus for determining the hardness of metal objects such as railway wheels.

In modern, high output foundries where upwards of 1,000 railway wheels are cast per day, it is desirable to provide a quick and accurate method for determining the Brinell hardness of such wheels. The present invention provides such method and an apparatus for carrying out the hardness testing operation.

In the method of hardness testing a metal object such as a railway wheel in accordance with the present invention, the wheel is rolled along a rail assembly into the testing device. The rail assembly is then lowered to place the wheel into a notched receiving assembly thereby providing longitudinal stability from rolling for the wheel. A movable frame brace is moved laterally into contact with the wheel hub pressing the back of the wheel into contact with frame supports. Accordingly, the wheel is laterally supported and is now ready for hardness testing.

A secondary frame assembly is movable about a pivot pin axis by the action of a hydraulic or pneumatic cylinder having one end affixed to a main frame of the testing assembly and the piston rod affixed to the end of the secondary frame assembly opposite from the end attached to the pivot axis. By extension and contraction of the piston assembly, the secondary frame can be moved about the pivot axis.

A grinding mechanism and a Brinell testing head are both affixed to the secondary frame in a manner such that rotation of the secondary frame about the pivot axis results in rotation of the grinding mechanism and Brinell testing head. The grinding mechanism and Brinell testing head are fixed in relation to each other such that upon rotation of the secondary frame, the grinding mechanism and Brinell testing head rotate an equal amount. Upon the lowering of the railway wheel to be tested into the notched receiving assembly, the secondary frame is rotated downwardly from the pivot axis to bring the grinding mechanism into contact with a portion of the rim of the railway wheel to thereby grind such portion. The secondary frame is then rotated upwardly to bring the Brinell testing head into general alignment with the area of the railway wheel previously ground. An additional clamping cylinder acts against the side of the railway wheel opposite the Brinell testing head to assure lateral stability of the railway wheel during the Brinell test. The Brinell testing head itself includes a cylinder mechanism by which it is mounted to the secondary frame. By movement of such cylinder, the Brinell head itself can be brought into contact with the railway wheel edge prior to the actual Brinell test. The hardness or Brinell test of the railway wheel is then performed in the usual manner by applying a known force to the testing head and determining the depth of penetration into the railway wheel. The hardness of the railway wheel is thusly quickly and accurately determined. Upon the withdrawal of the testing head by the action of its cylinder and the withdrawal of the clamping cylinder and frame support, the rail is once again raised to slightly lift the wheel out of the notched receiving assembly whereupon the wheel is rolled from the testing apparatus.

The grinding mechanism comprises a typical drive motor and wheel assembly, but also includes a wheel advancing mechanism similar to that disclosed in assignee's copending U.S. patent application Ser. No. 842,111, filed Mar. 20, 1986. Such a grinding wheel advancing mechanism assures that a uniform depth is ground into the railway wheel by allowing for the wear of the grinding wheel and slightly advancing radially outwardly such grinding wheel to account for such wear. In a manner disclosed in the copending application, the grinding wheel is radially outwardly advanced until a light beam is blocked indicating the exact radial extension of the grinding wheel desired whereupon the advancing mechanism is deactivated. When the grinding wheel is at such radial position, a uniform depth can be assured to be ground into the railway wheel to be hardness tested. Such grinding of the portion of the railway wheel to be tested is necessary to expose base metal to assure accurate hardness testing of the railway wheel.

BRIEF DESCRIPTION OF THE DRAWINGS

In the drawings,

FIG. 2 is a partial side view, in partial cross section, along lines 2—2, of the hardness testing device of the present invention.

DESCRIPTION OF THE PREFERRED EMBODIMENT

Figure 1:
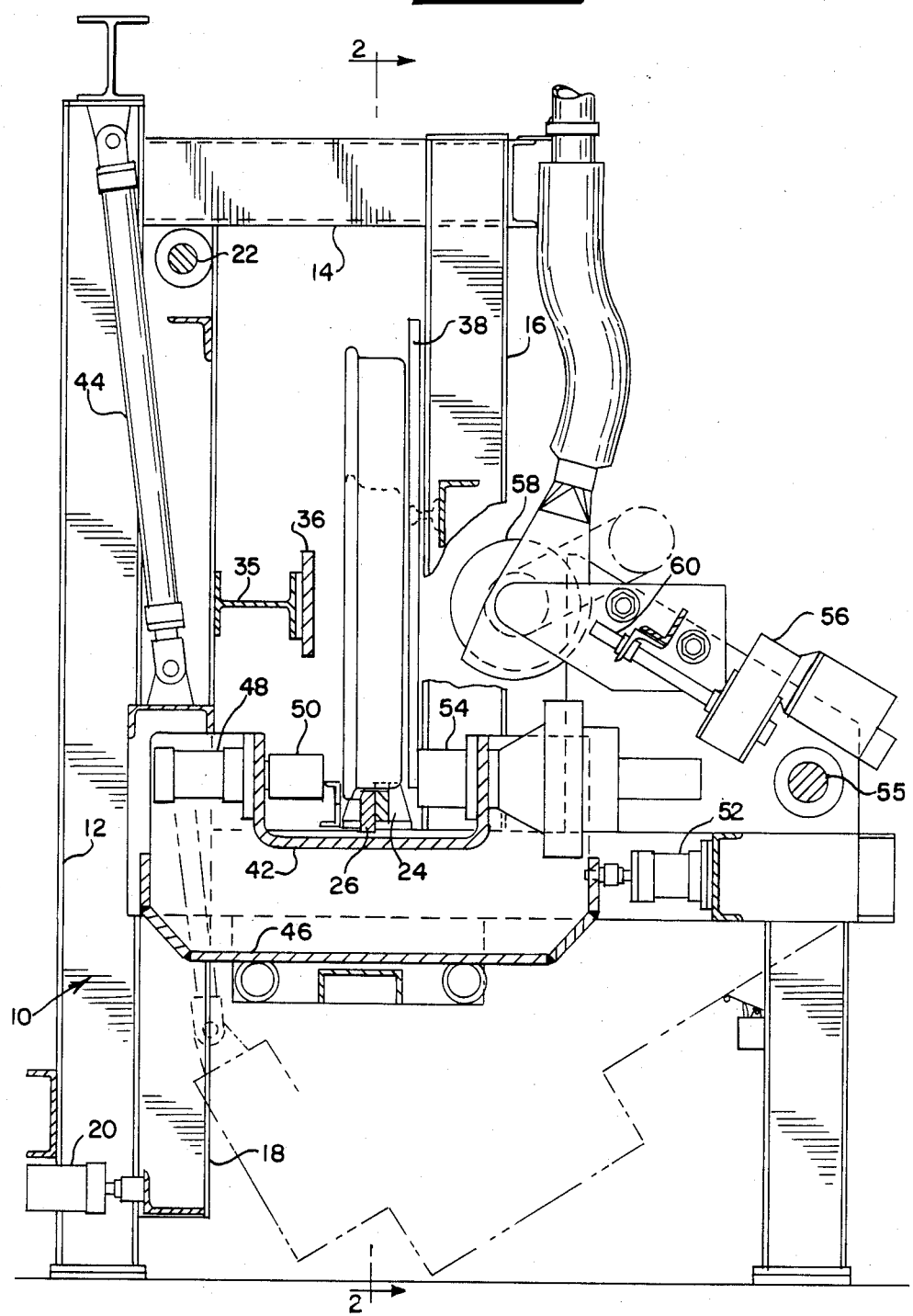
FIG. 1 is a front view, in partial cross section, of the hardness testing device of the present invention.

Referring now to FIGS. 1 to 2 of the drawings, one embodiment of the hardness testing apparatus of the present invention is shown generally at 10. Hardness testing apparatus 10 includes a main frame section comprising side beams 12 and 16 joined by upper beams 14. The main frame includes other structural beams not visible in the views offered in FIGS. 1 and 2. A railway wheel 30 is rolled into the main frame along track assembly 24. Track assembly 24 is supported at one end by a pivot mechanism 32 and at the other end by a piston assembly 34 extending from cylinder 36. Upon the lowering of piston 34, track section 24 also is lowered thereby dropping railway wheel 30 into a notched receiving assembly 26. Once in notched receiving assembly 26, the railway wheel is stabilized from rolling in a longitudinal direction. Notched receiving assembly 26 generally comprises a beam supported at one end by support assembly 27 and at its other end by support assembly 29. Upon the raising of piston 34, rail, assembly 24 lifts wheel 30 from notched receiving assembly 26 whereupon wheel 30 can be rolled out of the main frame of hardness testing apparatus 10.

A lateral wheel support assembly includes a beam 18 supported at its top end from a pivot point 22 and at its bottom end from a cylinder and piston assembly 20. Upon the extension of piston assembly 20, beam 18 is swung from pivot 22 in a counterclockwise direction toward the right in FIG. 1. Wheel support beam 35 is affixed to a position on the right side of beam 18 in the view shown in FIG. 1 and further includes a shimming mechanism 36 whereby various thicknesses of shims can be inserted to extend the length and reach of support beam 35. Upon such counterclockwise movement of beam 18, shim assembly 36 is brought into contact with wheel 30 and forces wheel 30 into contact with secondary support beams 38 and 40. Secondary support beams 38 and 40 are affixed to the main frame assembly in a manner such that upon movement of shim assembly 36 against wheel 30, wheel 30 is firmly supported in a lateral direction.

A secondary frame assembly comprises a base frame section 46 one end of which is supported by an extendable cylinder 52 which itself extends from a frame section supported about pivot shaft 55. The other end of base frame section 46 is supported by a piston extending from cylinder 44, with the other and of cylinder 44 being affixed to the main frame section of hardness testing apparatus 10 near upper beam section 14. Upon the extension of the piston from cylinder 44, base frame section 46 rotates about pivot shaft 55.

The two other components of the secondary frame assembly include wheel grinding apparatus 56 which comprises a grinding wheel 58 extending from shaft 60. Grinding device 56 includes sensing and motorization of shaft 60 such that grinding wheel 58 is adjustable to be extended. Grinding assembly 56 is part of the secondary frame assembly and accordingly pivots about shaft 55 with the movement of secondary frame base 46.

Also part of the secondary frame assembly is hardness or Brinell testing head 54. This hardness testing head is of a known design such that upon extension of cylinder 52 bringing hardness testing device 54 into contact with the edge of the railway wheel opposite support mechanism 50, a known force is applied to a penetrating assembly and the relative hardness of the railway wheel is determined by the depth of penetration of the device into the wheel.

The grinding assembly 56 and hardness testing assembly 54 are mounted in fixed relation to each other on the secondary frame assembly about pivot shaft 55. Upon the rotation of the secondary frame assembly, which includes support frame 42, clamping cylinder 48 and clamping piston 50 extending therefrom, by the extension of cylinder 44, grinding wheel 58 polishes a section of railway wheel 30. Upon the drawing of the shaft into cylinder 44, the secondary frame is swung in a clockwise direction about pivot 55 and the Brinell hardness testing head 54 is brought into general alignment with the ground section of railway wheel 30. Upon the clamping of the bottom section by the extension of clamping piston 50 from clamping cylinder 48, and the movement of hardness testing head 54 into contact with the lower right section of railway wheel 30 by the extension of cylinder 52, the hardness of the railway wheel is quickly and accurately determined.

Upon the withdrawal of the hardness testing head 54 from contact with the railway wheel 30 and the withdrawal of support head 50, rail assembly 24 is raised by the extension of piston 34 whereupon railway wheel 30 is raised from notched receiving assembly 26 and rolled from the hardness testing apparatus 10.

What is claimed is:

1. A hardness testing device comprising
   a main frame adapted to receive a metal wheel to be tested,
   adjustable bracing means to secure the metal wheel in the main frame,
   grinding means adapted to pass across a section of the metal wheel to grind said section,
   hardness means adapted to be brought into alignment with the ground section of the metal wheel to test the hardness of the metal wheel,
   a single pivot axis mounted on said main frame,
   a secondary frame to which said grinding means and said hardness testing means are mounted,
   and a clamping cylinder mounted to said secondary frame such that when said hardness testing means is in alignment with the ground section of the metal wheel, said clampng cylinder when extended contacts said wheel on a side opposite from said hardness testing means to provide lateral support to said wheel,
   wherein said secondary frame with said grinding means, said hardness testing means and said clamping cylinder are mounted to rotate about said single pivot axis, and said grinding means and said hardness testing means are mounted at a preslected angle to each other.

2. The hardness testing device of claim 1 further comprising a rail assembly upon which the wheel to be tested is rolled into the main frame,
   and a notched receiving assembly into which the wheel is lowered by the lowering of said rail assembly, said wheel being stabilized in a longitudinal direction when in said notched receiving assembly.

3. The hardness testing device of claim 1 further comprising
   an actuating cylinder secured at one end to said main frame and at a second end to said secondary frame,
   an adjusting cylinder having one end mounted to said secondary frame and a second end mounted to a movable section of said secondary frame,
   such that upon actuation of said actuating cylinder said secondary frame is rotated about said single pivot axis,
   and such that upon extension of said adjusting cylinder when said hardness testing device is in alignment with the ground section of said metal wheel, said movable section of said secondary frame is laterally moved such that said hardness testing device abuts said wheel.

4. The hardness hardness testing device of claim 1 further comprising support means against which said metal wheel can be abutted for lateral support thereof.

5. The hardness testing device of claim 4 wherein said adjustable bracing means comprises a horizontally extending support mounted to a laterally movable section of said main frame,
and a powered cylinder adapted to laterally move said section of said main frame such that said horizontally extending support contacts said metal wheel to abut said metal wheel against said support means to laterally stabilize said metal wheel.

* * * * *